United States Patent [19]
Miller

[11] 4,183,356
[45] Jan. 15, 1980

[54] OPHTHALMIC APPLICATOR DEVICE

[75] Inventor: Neil W. Miller, Pennsburg, Pa.

[73] Assignee: Merck & Co., Inc., Rahway, N.J.

[21] Appl. No.: 775,237

[22] Filed: Mar. 7, 1977

Related U.S. Application Data

[63] Continuation-in-part of Ser. No. 583,934, Jun. 5, 1975, abandoned.

[51] Int. Cl.² .............................................. A61M 31/00
[52] U.S. Cl. ..................................... 128/264; D24/23; D24/99
[58] Field of Search ............. 128/321, 264, 330, 340, 128/325, 355, 260; 46/29; 248/60, 64; 132/91; 238/10 E; D24/23, 99

[56] References Cited
U.S. PATENT DOCUMENTS

| D. 187,132 | 2/1960 | Griffin | 132/91 |
|---|---|---|---|
| 453,508 | 6/1891 | Ruby | 128/264 |
| 3,236,247 | 2/1966 | Brockman | 132/91 |
| 3,780,735 | 12/1973 | Crouter et al. | 128/223 |
| 3,789,845 | 2/1974 | Long | 128/264 |
| 3,828,777 | 8/1974 | Ness | 128/260 |
| 3,863,633 | 2/1975 | Ryde et al. | 128/260 |

FOREIGN PATENT DOCUMENTS

| 539186 | 4/1957 | Canada | 132/91 |
|---|---|---|---|
| 580091 | 7/1958 | Italy | 132/91 |
| 1342182 | 12/1973 | United Kingdom | 132/91 |

*Primary Examiner*—Robert W. Michell
*Assistant Examiner*—Arthur S. Rose
*Attorney, Agent, or Firm*—Edmunde D. Riedl; Raymond M. Speer

[57] ABSTRACT

An ophthalmic applicator device for mechanically inserting solid medicaments in the form of inserts into the cul-de-sac of the eye, comprising an elongated tip of non-toxic, pliable material terminating in a groove through an end of said tip sufficient to form two flexible, opposed termini of said tip whereby said insert is releasably gripped by frictional engagement between said termini; said groove having cross-sectional conformation and dimensions sufficient to releasably grip said insert, and at least one dimension sufficiently less than the greatest dimension of said insert to result in removal of said insert from the ophthalmic applicator device by contact of said insert with the cul-de-sac of the eye; and a handle attached to said tip at the end of said tip opposite said termini, and forming an interior angle therewith of from about 30° to about 120°.

5 Claims, 3 Drawing Figures

4,183,356

OPHTHALMIC APPLICATOR DEVICE

REFERENCE TO RELATED APPLICATIONS

This application is a continuation-in-part of Application Ser. No. 583,934, filed June 5, 1975, now abandoned.

BACKGROUND OF THE INVENTION

1. Field of the Invention

The usual treatment of various eye conditions consists of applying doses of appropriate medicaments in aqueous solutions, suspensions or ointments. While such treatments are satisfactory for treating eye conditions where only one or several applications of the medicinal agents are necessary, certain eye conditions require more frequent doses and the treatment is inconvenient to the patient. Recently, it has been proposed to apply the ophthalmically active medicinal agents in a solid form which will completely dissolve in the lacrimal fluid. See Loucas et al., J. of Pharm. Sci., Vol. 61, page 985, June 1972. The shape of the insert is not critical and may be in the form of a disc, oval, rectangle or rod. However, the rod-shaped insert is preferred, for reasons which will be described hereinafter.

The present invention relates to a mechanical ophthalmic instrument for eye therapy and more particularly to a mechanical instrument for inserting solid medicaments into the cul-de-sac or fornix of the eye.

The cul-de-sac or fornix of the eye is the vaultlike space from the eyelid to the eyeball, bounded by the conjuctiva, the delicate membrane that lines the eyelids and covers the exposed surface of the eyeball. There is, thus, a fornix behind both the lower eyelid and the upper eyelid, and these are termed the inferior conjuctival fornix and the superior conjuctival fornix, respectively.

2. Description of the Prior Art

The ophthalmic applicator device of the present invention is characterized by both safety and reliability. These characteristics are traceable, largely, to the pliable nature of the entire tip of the device, and to the absence of any moving parts in the device of the present invention. Prior art devices such as the one described in U.S. Pat. No. 3,828,777, which utilizes a minute suction cup, while without moving parts, presents serious problems of reliable release into the cul-de-sac of the eye. Other prior art devices which posses pliable jaws or tabs, such as those described in U.S. Pat Nos. 453,508 and 3,780,735, at the same time require the action of a plunger means for ejecting the medicament from the pliable end. Such devices present serious problems of safety and convenient operation in the environment of the delicate membranes forming the fornices fo the eye.

The ophthalmic applicator device of the present invention also possesses a unique juxtaposition of handle and tip portions to form an interior angle therewith of from about 30° to about 120°, which has been found essential to the safety and reliability which characterize the device of the present invention. By contrast, devices disclosed heretofore, such as that described in U.S. Pat. No. 3,863,633, show no appreciation of the importance of this unique configuration of the device of the present invention.

DETAILED DESCRIPTION OF THE INVENTION AND DRAWINGS

Figure 1:
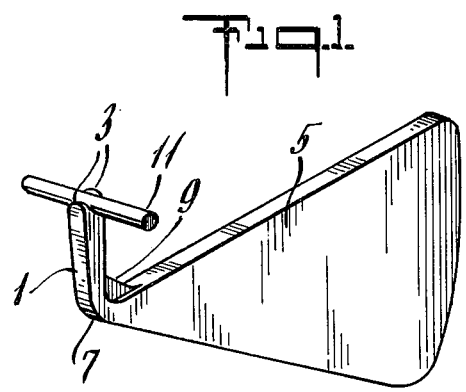
FIG. 1 is a perspective view of the ophthalmic applicator device (OAD).

FIG. 1 is a perspective view of the ophthalmic applicator device which comprises an elongated tip 1 of a non-toxic, pliable material. The tip 1 is about 5 to 15 mm in length and terminates in a groove through the end of said tip sufficient to form two flexible, opposed termini 3 to releasably grip an insert 11 by frictionally engaging the insert 11 between the termini 3. An insert of preferred rod-shaped configuration is illustrated. A handle 5 is attached to said tip at the end opposite the termini 3 at an interior angle of from about 30° to 120°, measured between the major axes of the handle and tip, preferably 45° to 90° and especially at about 70°. A reinforcing rib 9 permits suitable pliability in the tip portion, while at the same time assuring the proper configuration angle between the tip portion and the handle.

Figure 2:
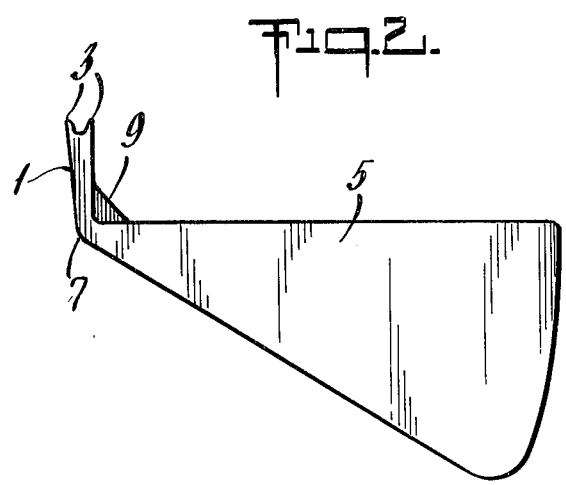
FIG. 2 is a top view of the device.

FIG. 2 is the top view of the ophthalmic applicator device which indicates an embodiment of the handle 5. The shape of the handle 5 is not critical, and in this embodiment is formed of a planar element in the form of a segment of a circle and which is attached to one end of the tip 1 at that portion of the segment corresponding to the center of the circle 7. The portion of the handle 5 corresponding to the periphery of a segment of a circle is of sufficient size to allow the person inserting the medicament into the eye to easily grasp the handle. The length of the handle is not critical and is generally from about 25 to 75 mm in length, preferably 40 to 60 mm. The angle of the segment of the circle is not critical and generally is from about 15° to 45° and preferably 25° to 35°. The thickness of the handle is not critical, and generally would be dependent upon the modulus of the material employed in the construction of the ophthalmic applicator device, generally from about 1.5 to 2.5 mm, preferably about 2.0 mm. The material from which the handle is constructed is not critical, and it is not required that the handle be constructed of pliable material. When ophthalmic inserts of differing dosage concentrations, or containing different ophthalmic medicaments, are used by the same patient, the inserts would desirably be of different size, thus requiring different applicator devices, and it would be desirable in that case to provide applicator devices having handles sufficiently different in configuration, color, texture, and so forth, as to enable said patient to readily distinguish between the devices, and thus the inserts, being used. As already stated, a reinforcing rib 9 may be used to immobilize the tip 1 so that the angle between the tip 1 and the handle 5 remains constant. All edges of the device may be rounded to minimize the possibility of accidental injury to the eye while inserting the medicament.

Figure 3:
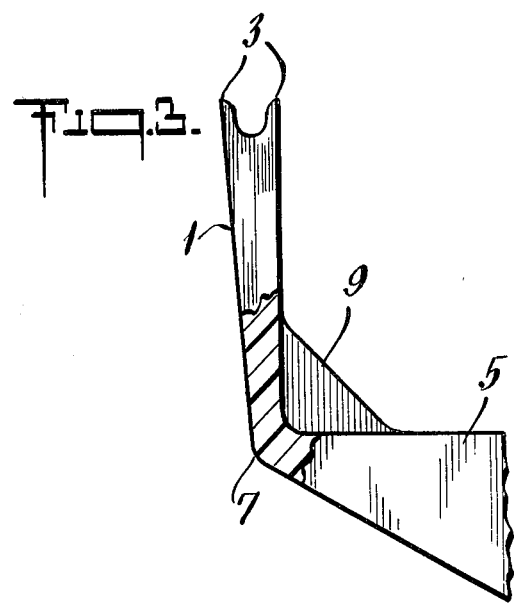
FIG. 3 is an enlarged top view of the tip of the device.

FIG. 3 is an enlarged top view of the tip 1 of the applicator highlighting the position of the termini 3. The two opposed termini 3 are formed by and separated by an arcuate groove, which is a preferred configuration, running their entire width, i.e., the horizontal dimension of the tip 1. The groove has cross-sectional conformation and dimensions sufficient to releasably grip the ophthalmic insert, and at least one dimension sufficiently less than the greatest dimension of said insert to result in removal of said insert from the ophthalmic applicator device by contact of said insert with the cul-de-sac of the eye. By having at least one dimension of the groove less than the greatest dimension of the insert which the applicator device is being used to administer, said insert will be caused to extend beyond or overhang the tip of the applicator device. Thus situated, said insert, during administration, will contact and be held by the tissues of the cul-de-sac of the eye, and will be removed from the applicator device, where it has been releasably gripped by the combined action of the groove and termini. It will be appreciated, of course, that injury to the delicate tissues of the cul-de-sac must be avoided, while at the same time they must be contacted by the insert being releasably held by the applicator device. This dual objective is accomplished by combined action of the pliable nature of the tip and flexible action of the termini, as well as the cross-sectional conformation and dimensions of the groove, whereby the insert is releasably held by the applicator device with only sufficient force to accomplish transport and administration of the insert, but insufficient force to prevent release of the insert on gentle contact with the tissues of the cul-de-sac.

The cross-sectional conformation of the groove may be varied, but should be adapted to the shape of the insert being administered. Thus, the conformation of the groove may be arcuate, parabolic, triangular, rectangular, and so forth, to coincide with essentially the same cross-sectional conformation of the insert to be administered. In the present invention, it is preferred to employ rod-shaped inserts, for reasons explained hereinafter, and for such an insert, having a circular cross-section, it is preferred to employ a groove of arcuate cross-sectional conformation in the ophthalmic applicator device.

The groove is from about 0.5 to 2.0 mm in depth, and from about 0.5 to 1.5 mm in width or diameter between the termini of the device, and is preferably slightly smaller than the shape of the insert, thereby enabling the termini 3 to releasably grip said insert by frictionally engaging the insert between the two termini 3. Nevertheless, a film of water surrounding the termini and groove, introduced during recommended sterilization of the applicator device with hot water before usage, may permit the termini to releasably grip an insert the same size as, or slightly smaller than the groove. The shape of the insert is not critical. However, a preferred embodiment of the insert is one which is cylindrical in shape (rod-like) with a diameter of from about 0.5 to 1.5 mm and a length of from about 2 to 12 mm. For such a preferred rod-shaped insert, use of an applicator device having a groove with an arcuate cross-sectional conformation is preferred.

The preferred shape or conformation of the groove of the applicator device of the present invention has been described as "arcuate". This term has reference to the cross-sectional conformation of the groove, and is intended to describe said conformation as essentially approximating an arc of a circle, usually through 180°.

The termini 3 are preferably approximately equal in size and are integrally molded into the pliable tip 1. The termini 3 may be from about 1.0 to 3.0 mm in width, preferably 1.5 to 2.5 mm and especially 2.0 mm; from about 0.5 to 2.0 mm in depth, preferably 1.0 to 1.5 mm and especially 1.0 mm; and from about 0.2 to 0.8 mm in thickness, preferably 0.3 to 0.6 and especially 0.4 mm. The gripping (inner) surface of the termini is not critical and may be smooth, notched, wavelike, or irregular. The tip is from about 5 to 15 mm in length, preferably 9 to 11 mm and especially 9 to 10 mm, so as to enable the user of the insert to insert the medicament into the proper area of the cul-de-sac or fornix of the eye without assistance, but sufficiently deeply placed to prevent dislodgement. Where the insert is to be placed or lodged in the superior fornix, the tip must be longer than the tip required for lodging an insert in the inferior fornix. The length, width and thickness of the tip will thus be essential to proper and safe operation of the applicator device of the present invention. These dimensions must also be sufficient to maintain the shape of the tip in the absence of external forces, but also not too great to permit the tip readily deform upon application of mild forces such as would be encountered upon contact with the eye ball or the surrounding tissues of the cul-de-sac.

The tip may be from about 3.0 to 6.0 mm in width at the portion attached to the handle, preferably 4.0 to 5.0 mm tapering to about 1.0 to 3.0 mm at the tip containing the termini, preferably about 2.0 mm, and from about 1.5 to 3.0 mm in height or thickness, and may be tapered so that the thickest portion is at the end of the tip containing the termi. The end of the tip containing the termini should be of such dimensions that the termini may be molded as part of the tip. The tip 1 is attached to the handle 5 at the end opposite the termini 3. A reinforcing rib 9 may be present.

The ophthalmic applicator device may be produced in one-piece by suitable forming techniques such as compression molding and especially injection molding. The tip 1 and handle 5 may be produced wherein the tip and the handle are in different planes, or preferably in the same plane to facilitate packaging of the device.

The tip portion of the ophthalmic applicator device of the present invention must be pliable. The term "pliable" is intended to describe the property or characteristic of the tip portion wherein: (1) it is supple enough to bend freely and repeatedly without breaking; (2) it yields readily to the tissues of the cornea and cul-de-sac of the eye, thus avoiding injury thereto; and yet (3) it possesses sufficient rigidity to maintain its shape in the absence of external forces and while gripping, transporting, and lodging an ophthalmic insert being administered with the ophthalmic applicator device of the present invention.

The ophthalmic applicator device may be produced from a non-toxic, pliable material which is not readily water soluble, does not support the growth of microorganisms and is readily sterilized, such as a silicone rubber composition and especially a thermoplastic elastomer composition. Thermoplastic elastomer polymers behave like thermoplastic materials above their softening point and may be processed in ordinary thermoplastic processing equipment. The thermoplastic rubber composition comprises a block copolymer comprising styrene units strung together in sequence, followed by a large number of diene units such as butadiene or isoprene, followed by another section of styrene units at the end. The block copolymer may be partially hydrogenated as described in U.S. Pat. No. 3,595,942. The thermoplastic rubber compositions may be obtained and used as the gum polymer or as a composition comprising the polymer and in addition one or more of the following items: a processing and flow promoting aid such as a rubber processing oil, a resin such as a polyethylene or a polystyrene, a stabilizer such as one of the hindered phenols or an unsaturated ester and a filler such as a clay, a silica or a carbon black. Such termoplastic rubbers are commercially produced and marketed as Phillips Petroleum's Solprene ®, Uniroyal's TPR ® and Shell Chemical's Kraton ® Thermoplastic rubbers. One such thermoplastic rubber which may be used in Shell Chemical's Kraton ® G-2705 thermoplastic rubber (formerly GX-7050) which is a thermoplastic rubber composition comprising a partially hydrogenated block copolymer as described in U.S. Pat. No. 3,595,942, a processing aid (such as a rubber processing oil) and a stabilizer (such as a hindered phenol or an unsaturated ester). The material used in the construction of the device should be easily sterilized by common methods such as immersion in a 0.01% aqueous benzalkonium chloride solution, 70% isopropanol solution or running hot water (45° to 70° C.) for 10 to 30 seconds.

Typically in the use of the ophthalmic applicator device, the hands of the person inserting the device should be thoroughly washed with soap and water. The applicator device is then sterilized by holding it under running hot water for 15 seconds and shaking off the excess water. Placing the handle 5 of the applicator between the thumb and middle finger with the forefinger located near the end of the handle attached to the tip, the tip 1 of the applicator incorporating the groove is gently pressed onto the insert. The ophthalmic insert will adhere to the applicator. Looking into a mirror and using the free hand to gently grasp the surface of the outer one-third of the lower lid between the thumb and index (fore) finger, the eye lid is pulled away from the eye ball creating a pocket between the eye ball and the eye lid. The tip 1 of the applicator containing the ophthalmic insert is placed into the pocket created between the lid and the eye ball over the white part of the eye (sclera), keeping away from the colored part of the eye (cornea). The applicator device is removed and the ophthalmic insert, held by the tissues of the cul-de-sac or fornix of the eye, remains behind. To insure proper placement in the eye, after removing the applicator device, the lower lid should be pulled out and up and over the ophthalmic insert while looking down by grasping the skin surface of the outer one-third of the lower lid between the thumb and index finger. A properly positioned insert resides in the lower portion of the eye behind the lower lid.

In a similar manner, where the ophthalmic insert is to be administered to the upper cul-de-sac, or superior fornix, of the eye, the upper lid is pulled out, down, and over the ophthalmic insert while looking up. As previously described, for administration of an ophthalmic insert to the superior fornix of the eye, the ophthalmic applicator device of the present invention will preferably have a tip portion which is longer than the tip portion employed for administration of an ophthalmic insert to the inferior fornix of the eye. In addition, for such administration to the superior fornix, the ophthalmic applicator device will have the handle attached to the tip portion at an interior angle which is obtuse, that is, from about 90° to 120°.

While the ophthalmic applicator device described above is suitable for administering ophthalmic inserts of a variety of shapes, the use of the applicator device with a rod-shaped insert is preferred. This preference arises from the superior ability of a rod-shaped insert to remain lodged in the cul-de-sac of the eye, and also from inability of a rod-shaped insert to be administered to the eye by means of the ophthalmic applicator device in any manner except by way of being gripped through its shortest dimension whereby injury to the tissues forming the cul-de-sac of the eye is avoided. Use of the rod-shaped ophthalmic insert thus permits safe, consistent, and permanent lodging of the insert within the cul-de-sac of the eye.

While there have been described and pointed out the fundamental novel features of the invention as applied to the preferred embodiments, those skilled in the art will appreciate that various changes and modifications and omissions fom the ophthalmic instrument for eye therapy described herein can be made without departing from the spirit of the invention. It is the intention, therefore, to be limited only by the scope of the claims which follow.

What is claimed is:

1. An ophthalmic applicator device for mechanically inserting solid medicaments, in the form of an ophthalmic insert, behind the upper or lower eye lid and into the upper or lower cul-de-sac of the eye consisting of:

an elongated handle portion having a major axis and a tip portion;

said tip portion having only one elongated tip of non-toxic, pliable material, said tip terminating in a single groove through an end of said tip sufficient to form two flexible, opposed termini of said tip adapted to releasably grip an insert by frictional engagement thereof between said termini, one of said termini being located at a distance further from the handle than the other of said termini;

said groove having cross-sectional conformation and dimensions of a size and shape sufficient to releasably grip an ophthalmic insert, and at least one dimension sufficiently less than the greatest dimension of an ophthalmic insert to result in removal of an ophthalmic insert from the ophthalmic applicator device by contact of an ophthalmic insert with the cul-de-sac of the eye; and said handle portion attached to said tip portion at the end of said tip portion opposite said termini, and forming an interior angle between the axis of said elongated tip and the major axis of the elongated handle therewith of from about 30° to about 120°.

2. The ophthalmic applicator device of claim 1 wherein said handle forms an interior angle with said tip of from about 45° to about 90°.

3. The opthalmic applicator device of claim 1 wherein the cross-sectional conformation of said groove is arcuate.

4. The ophthalmic applicator device of claim 1 wherein said device has the tip portion having a length, a width and a height, said tip portion having a length of from about 5 to 15 mm, having a width of from about 1.0 to 3.0 mm at the end and having a height of from about 1.5 to 3.0 mm; a groove in said tip portion said groove having an arcuate cross-sectional conformation, of from about 0.5 to 1.5 mm in width or diameter between the termini of the device, and from about 0.5 to 2.0 mm in depth; two equal-sized termini of from about 1.0 to 3.0 mm in width, 0.5 to 2.0 mm in depth and 0.2 to 0.8 mm in thickness; and a handle of from about 25.0 to 75.0 mm in length.

5. The ophthalmic applicator device of claim 1 wherein said device has a tip portion of from about 9 to 11 mm in length, having a width of from about 1.2 to 2.0 mm at the end, containing a groove having an arcuate cross-sectional conformation, having a diameter of from about 0.5 to 1.5 mm; termini of from about 1.5 to 2.5 mm in width, from about 1.0 to 1.5 mm in depth and from about 0.3 to 0.6 mm in thickness, and said handle of from about 40 to 60 mm in length.

* * * * *